United States Patent [19]
Abou-Gharbia et al.

[11] Patent Number: 4,910,302
[45] Date of Patent: Mar. 20, 1990

[54] PSYCHOTROPIC POLYCYCLIC IMIDES

[75] Inventors: Magid A. Abou-Gharbia, Glen Mills; Gary P. Stack, Merion, both of Pa.

[73] Assignee: American Home Products Corporation, New York, N.Y.

[21] Appl. No.: 286,576

[22] Filed: Dec. 19, 1988

[51] Int. Cl.$^4$ ............... C07D 471/00; C07D 209/56; C07D 487/04; C07D 223/16
[52] U.S. Cl. ................... 540/486; 540/521; 546/68; 548/424
[58] Field of Search ............ 548/424; 546/68; 540/468, 485, 521

[56] References Cited

U.S. PATENT DOCUMENTS 3,944,549 3/1976 Laflon .............................. 546/376
3,993,662 11/1976 Brechbuhler et al. ............ 548/424
4,061,763 12/1977 Shepard et al. ................... 548/424

OTHER PUBLICATIONS

Derwent Abstract-87-118063/17 of GB 2,181,731.
Abstract of U.S. Pat. No. 3,993,662–Nov. 23, 1976.
Derwent Abstract-76-30495X/17 of German 2,544,382.
Fozard et al., Br. J. Pharmacol 90, 273 P (1987).

Primary Examiner—Mukund J. Shah
Assistant Examiner—E. C. Ward
Attorney, Agent, or Firm—Richard K. Jackson

[57] ABSTRACT

Compounds of the formula:

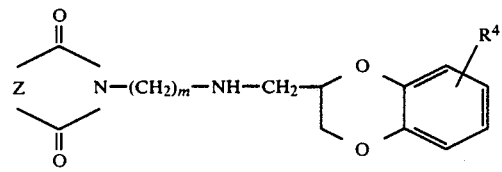

in which Z is

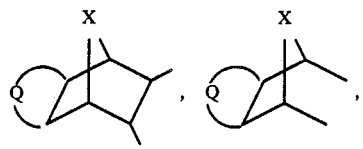

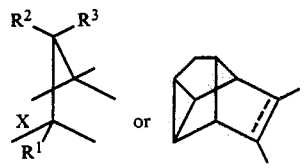

wherein X is alkylene, ethanylene or alkylidene; Q is alkylene, alkylidene,

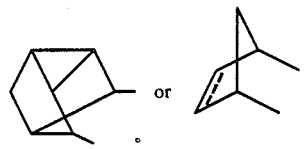

or Q, taken together with the carbon atoms to which it is attached forms a benzene ring or a substituted benzene ring, in which said substituents are —OH, —OCH$_3$, alkyl, halo, —CF$_3$, —NH$_2$, monoalkylamino, dialkylamino or alkanoylamino; R$^1$ is hydrogen or alkyl; R$^2$ and R$^3$ are, independently, hydrogen or alkyl or taken together with the carbon atoms to which they are attached, they form a cycloalkane or cycloalkene ring; m is one of the integers 2-5; R$^4$ is hydrogen, hydroxy, cyano, alkyl, alkoxy, halo, amino, alkylamino, phenylamino, tolylamino, xylylamino, mesitylamino, methoxyphenylamino, or halophenylamino; and the dotted lines represent optional unsaturation; or a pharmaceutically acceptable salt thereof.

11 Claims, No Drawings

PSYCHOTROPIC POLYCYCLIC IMIDES

BACKGROUND OF THE INVENTION

Japanese Patent No. 60/87262 (C.A. 103: 215155k) discloses N-(heteroaryl-piperazinylalkyl)cycloalkanosuccinimide derivatives as having anticonflict activity.

Fozard et al., Br. J. Pharmacol. 90, 273P (1987) disclose 8-[4-(1,4-benzodioxan-2-ylmethylamino)butyl]-8-azaspiro[4.5]decane-7,9-dione (MDL 72832) as a selective and stereospecific [-(MDL) 72832 bonds 32 times as much as the dextro rotatory isomer at the 5-HT$_{1A}$ receptor site] ligand for 5-HT$_{1A}$ receptors.

DESCRIPTION OF THE INVENTION

In accordance with this invention, there is provided a group of antipsychotic/anxiolytic agents of the formula:

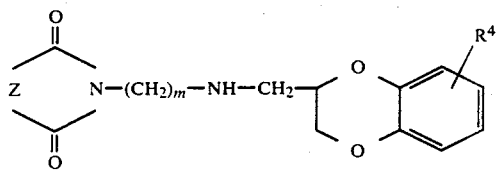

in which
Z is

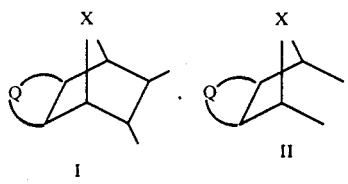

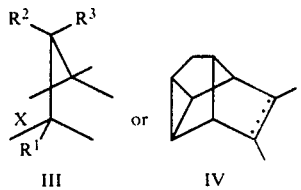

wherein
X is alkylene of 1 to 4 carbon, ethenylene atoms or alkylidene of 2 to 4 carbon atoms;
Q is alkylene of 1 to 4 carbon atoms, alkylidene of 2 to 4 carbon atoms,

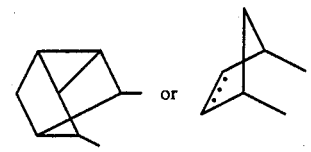

or Q, taken together with the carbon atoms to which it is attached forms a benzene ring or a substituted benzene ring, in which the substituent is —OH,—OCH$_3$, alkyl of 1 to 3 carbon atoms, halo, —CF$_3$, —NH$_2$, monoalkylamino, in which the alkyl substituent contains 1 to 3 carbon atoms, dialkylamino in which each of the alkyl substituents contains 1 to 3 carbon atoms, or alkanoylamino in which said alkanoyl group contains 2 to 4 carbon atoms;

R$^1$ is hydrogen or alkyl of 1 to 3 carbon atoms;
R$^2$ and R$^3$ are, independently, hydrogen or alkyl of 1 to 3 carbon atoms, or taken together with the carbon atom to which they are attached, they form a cycloalkane or cycloalkene ring of 3 to 7 carbon atoms;
m is one of the integers 2, 3, 4, or 5;
R$^4$ is hydrogen, hydroxy, cyano, alkyl of 1 to 3 carbon atoms, alkoxy of 1 to 3 carbon atoms, halo, —NHR$^5$ where R$^5$ is H, alkyl of 1 to 3 carbon atoms, phenyl, tolyl, xylyl, mesityl, methoxyphenyl or halophenyl;
and
the dotted line represents optional unsaturation; or a pharmaceutically acceptable salt thereof.

Of these compounds, the preferred members are those in which X is ethylene or ethenylene when Z is I or III, methylene when Z is II and R$^4$ is optimally hydrogen, hydroxy, or methoxy. The halo substituent may be fluoro, chloro, bromo, or iodo, but chloro and bromo are most preferred.

The pharmaceutically acceptable salts are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

The compounds of this invention are prepared by conventional methods. For example, a polycylic 1,2 or 1,3-dicarboxylic acid or anhydride derived therefrom is refluxed with the desired [2,3-dihydro-1,4-benzodioxan-2-ylmethylamino]alkylamine in dry pyridine, toluene or xylene. Water removal may be achieved by either chemical (e.g. ethoxyacetylene) or mechanical (e.g. Dean-Stark trap) means. Alternatively, the compounds of this invention are readily prepared from the analogous polycyclic imide via alkylation with a suitable dihalo-lower-alkane in the presence of a strong base such as sodium hydride followed by reaction of the intermediate product with the desired benzodioxanmethyl amine, thusly:

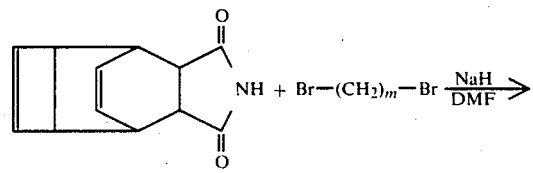

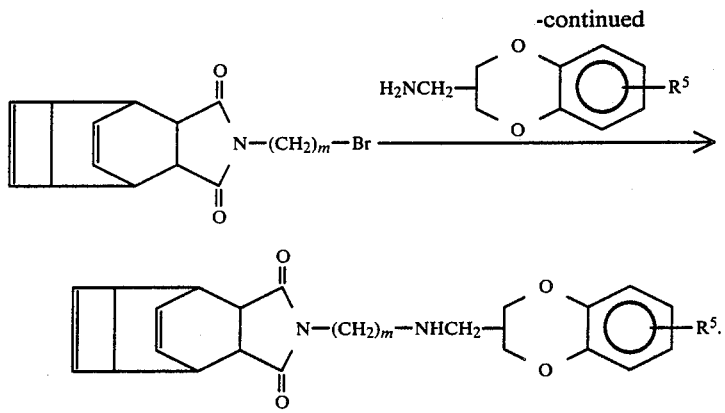

The polycyclic dicarboxylic acids themselves are known compounds or they can be prepared from the appropriate polycyclic olefin by treatment with a suitable oxidizing agent such as potassium permanganate or ruthenium tetroxide (or from the appropriate polycyclic ketone by treatment with potassium permanganate or potassium trioxide or from the appropriate diketone via treatment with periodic acid). These procedures may be illustrated as follows:

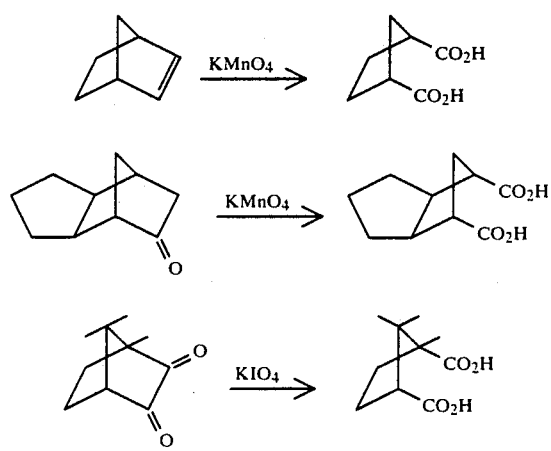

The compounds of this invention possess high affinities for the dopamine D-2 receptor and the serotonin 5-HT$_{1A}$ receptor, and consequently, they are useful as antipsychotic and anxiolytic agents for the treatment of a variety of central nervous system disorders such as paranoia, schizophrenia, anxiety, sleep disorders, and related problems.

High affinity for the dopamine D-2 receptor was established by the standard experimental test procedure of Fields et al., Brain Res., 136 578 (1977) and Yamamura et al., eds., Neurotransmitter Receptor Binding, Raven Press, N.Y. (1978) wherein homogenized limbic brain tissue is incubated with $^3$H-spiroperidol and various concentrations of test compound, filtered and washed and shaken with Hydrofluor scintillation cocktail (National Diagnostics) and counted in a Packard 460 CD scintillation counter. The results of this testing with compounds representative of this invention is given below.

High affinity for the serotonin 5-HT$_{1A}$ receptor was established by testing the claimed compounds ability to displace [$^3$H] 8-OHDPAT (dipropylaminotetralin) from the 5HT$_{1A}$ serotonin receptor following the procedure of Hall et al., J. Neurochem. 44 1685 (1985). This procedure is employed to analogize this property of the claimed compounds with that of buspirone, which is a standard for anxiolytic activity, and, like the compounds of this invention, displays potent affinity for the 5-HT$_{1A}$ serotonin receptor subtype. The anxiolytic activity of buspirone is believed to be, at least partially, due to its 5-HT$_{1A}$ receptor affinity (Vander Maclen et al., Eur. J. Pharmacol. 1986, 129 (1-2) 133-130.

The results of the two standard experimental test procedures described in the preceding two paragraphs was as follows:

| Compound | D-2 Binding (% Inhibition at 1 μM) | 5-HT$_{1A}$ Binding (% Inhibition at 1 μM) |
|---|---|---|
| Example 1 | 100 | 96 |
| Example 2 | 100 | 96 |
| Example 3 | 100 | 94 |
| Example 4 | 100 | 100 |
| Example 5 | 100 | 100 |
| Example 6 | 61 | 52 (0.1 μM) |
| Example 7 | 54 | 92 (0.1 μM) |
| Example 8 | 89 | 100 (0.1 μM) |

Hence, the compounds of this invention are useful in the treatment of multi-CNS disorders amenable to treatment with antipsychotic and anxiolytic agents. They may be administered neat or with a pharmaceutical carrier to a patient in need thereof by the attending physician. The pharmaceutical carrier may be a solid or a liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be by either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis or state of anxiety and the size, age and response pattern of the patient.

The following examples illustrate the production of representative compounds of this invention.

EXAMPLE 1

Decahydro-3-[4-[(2,3-dihydro-1,4-benzodioxan-2-ylmethyl)amino]butyl]-1,5-methano-6,7,9-metheno-2H-pentaleno[1,2-d]azepine-2,4(3H)-dione 2-Chloromethylbenzodioxan (18.5 g, 0.10 mole) and 1,4-diaminobutane (25 g, 0.30 mole) were combined in 500 ml of N-methylpyrolidinone and heated at 100° C. for 24 hours. The solvent and excess diaminobutane were removed in vacuum and the product was dissolved in water and desalted by passing it through an Amberlite® basic ion exchange resin. The aqueous solution was extracted three times with 350 ml portions of ethyl acetate. The combined organic extracts were dried over $Na_2SO_4$, filtered, and evaporated to yield 20.5 g of 4-[(2,3-dihydro-1,4-benzodioxan-2-ylmethyl)amino]butylamine.

4.7 Grams (20 mmole) of the amine prepared above was dissolved in 200 ml of xylene and 4.6 g (20 mmole) of decahydro-1,5methano-6,8,9-methenopentaleno[1,2-d]oxepine-2,4(1H, 5H)-dione in 50 ml of methylene chloride was added. The lower boiling solvent was distilled off and the mixture was refluxed for 48 hours with water removal via a Dean-Stark trap. The solvent was removed in vacuum and the residue was dissolved in chloroform and filtered through 75 g of silica gel. Concentration in vacuum and recrystallization from 100 ml of isopropanol by addition of 10 ml of 4N isopropanolic HCl gave 2.0 g of the title compound, monohydrochloride, quarter hydrate, as a white solid (m.p. 153°–155° C.).

Elemental analysis for: $C_{27}H_{32}N_2O_4 \cdot HCl \cdot \frac{1}{4}H_2O$
Calc'd: C, 66.25; H, 6.90; N, 5.72
Found: C, 66.23; H, 7.00; N, 5.41

EXAMPLE 2

Endo-2-[4-[(2,3-dihydro-1,4-benzodioxan-2-ylmethyl)amino]butyl]octahydro-4,5,7-metheno-1H-pentaleno[1,2-c]pyrrole-1,3(2H)-dione Octahydro-4,5,7-methenopentaleno[1,2-c]furan-1,3-dione (5.7 g, 30 mmoles) was combined with b 7.0 g (30 mmole) of 4-[(2,3-dihydro-1,4-benzodioxan-2-ylmethyl)amino]butylamine in 200 ml of xylene and refluxed for 48 hours with water separation via a Dean-Stark trap. The solvent was removed in vacuum and the residue chromatographed on silica gel with chloroform as the eluent to give 2.0 g of the more polar endo imide plus a mixture of exo and endo isomers. The mixture was rechromatographed on 100 g of silica gel with chloroform and this time gave 2.3 g of pure endo isomer plus a mixture now enriched with the exo imide. The fractions enriched with the endo isomer were combined in 100 ml of isopropanol and 4 ml of 4N isopropanolic HCl was added, followed by 300 ml of diethyl ether. The title compound was obtained as a white crystalline solid, 3.4 g (m.p. 190°–191° C.).

Elemental analysis for: $C_{24}H_{28}N_2O_4 \cdot HCl$
Calc'd: C, 64.78; H, 6.57; N, 6.30
Found: C, 64.78; H, 6.55; N, 6.15

EXAMPLE 3

Exo-2-[4-[(2,3-dihydro-1,4-benzodioxan-2-ylmethyl)amino]butyl]octahydro-4,5,7-metheno-1H-pentaleno[1,2c]pyrrole-1,3(2H)-dione The column fraction from Example 2 which had been enriched in the minor (exo) isomer was rechromatographed on 100 g of silica gel with chloroform to give 1.5 g of pure exo imide. This was recrystallized from a mixture of 75 ml of isopropanol and 250 ml of diethyl ether with addition of 3 ml of 4N isopropanolic HCl to give 1.0 g of white, solid monohydrochloride (m.p. 206°–208° C.).

Elemental analysis for: $C_{24}H_{28}N_2O_4 \cdot HCl$
Calc'd: C, 64.78; H, 6.57; N, 6.30
Found: C, 64.74; H, 6.58; N, 6.28

EXAMPLE 4

2-[4-[(2,3-Dihydro-1,4-benzodioxan-2-ylmethyl)amino]butyl]hexahydro-4,7-etheno-1H-cyclobut[f]isoindole-1,3-(2H)-dione Hexahydro-4,7-etheno-1H-cyclobut[f]isobenzofuran-1,3(2H)-dione (6.1 g; 0.03 mole) and 4-[(2,3-dihydro-1,4-benzodioxan-2-ylmethyl)amino]butylamine (7.0 g; 0.03 mole) were refluxed in dry pyridine (40 ml) overnight. The pyridine was evaporated under reduced pressure and the remaining known residue was dissolved in 200 ml of methylene chloride. The methylene chloride solution was washed with water, dried over anhydrous sodium sulfate and evaporated. The residue was chromatographed on silica gel using ethylacetate as the eluent to afford 6 g of the title compound. The free base was converted to the hydrochloride salt with isopropanolic HCl (m.p. 224° C.).

Elemental analysis for: $C_{25}H_{28}N_2O_4 \cdot HCl$
Calc'd: C, 65.71; H, 6.40; N, 6.13
Found: C, 65.31; H, 6.19; N, 6.04

EXAMPLE 5

2-[4-[2,3-Dihydro-1,4-benzodioxan-2-ylmethyl)amino]-butyl]hexahydro-4,6-etheno-cycloprop[f]isoindole-1,3-(2H,3aH)-dione Hexahydro-4,6-etheno-cycloprop[f]benzofuran-1,3-(2H,3aH)dione (2.35 g; 0.013 mole) and 4-[(2,3-dihydro-1,4-benzodioxan-2-ylmethyl)amino]butylamine (3.77 g; 0.016 mole) were refluxed in dry pyridine (40 ml) overnight. The title compound was separated and worked up by the procedure of Example 4 to obtain the monohydrochloride salt (m.p. 198°–200° C.).

Elemental analysis for: $C_{24}H_{28}N_2O_4 \cdot HCl$
Calc'd: C, 64.79; H, 6.52; N, 6.30
Found: C, 64.86; H, 6.42; N, 6.21

EXAMPLE 6

3-[2-[[(2,3-Dihydro-1,4-benzodioxan-2-ylmethyl)amino]ethyl]-1,8,8-trimethyl-3-azabicyclo[3.2.1]octane-2,4-dione 2-Chloromethylbenzodioxan (18.5 g, 0.10 mole) and ethylene diamine (30 g, 0.50 mole) were combined in 500 ml of N-methylpyrrolidinone and heated at 80° C. under nitrogen for 24 hours. The solvent and excess ethylenediamine were removed in vacuum and the product was dissolved in water and desalted by passing it through an Amberlite ® basic ion exchange resin. the aqueous solution was concentrated in vacuum to give 16 g of 2-[(2,3-dihydro-1,4-benzodioxan-2-ylmethyl)amino]ethylamine.

2.1 Grams (10 mmole) of the amine prepared above was dissolved in 100 ml xylene and 1.8 g (10 mmole) of (IR, 3S)-camphoric anhydride was added. The mixture was refluxed under nitrogen for 48 hours with water removal via a Dean-Stark trap. The solvent was removed in vacuum and the residue was column chromatographed on 100 g of silica gel with chloroform as eluent. Crystallization from isopropanol with the addition of 4N isopropanolic HCl gave 1.9 g of hydrochloride (m.p. 174°–175° C.).

Elemental analysis for: $C_{21}H_{28}N_2O_4 \cdot HCl$
Calc'd: C, 61.68; H, 7.15; N, 6.85
Found: C, 61.62; H, 6.89; N, 6.82

EXAMPLE 7

2-[2-[(2,3-Dihydro-1,4-benzodioxan-2-ylmethyl)amino]ethyl]hexahydro-4,7-etheno-1H-cyclobut[f]isoindole-1,3-(2H)-dione To 2.1 g of 2-[(2,3-dihydro-1,4-benzodioxan-2-ylmethyl)amino]ethylamine (10 mmoles) in 100 ml of xylene was added 2.0 g (10 mmoles) of hexahydro-4,7-etheno-1H-cyclobut[f]isobenzofuran-1,3(2H)-dione and the mixture was refluxed under $N_2$ for 48 hours with water removal via Dean-Stark trap. After cooling the mixture was column chromatographed on 100 g of silica gel with chloroform as eluent. Crystallization from isopropanol with the addition of 4N isopropanolic HCl gave 2.1 g of hydrochloride (m.p. 237°–238° C.).

Elemental analysis for: $C_{23}H_{24}N_2O_4 \cdot HCl$
Calc'd: C, 64.41; H, 5.88; N, 6.53
Found: C, 64.72; H, 5.84; N, 6.53

EXAMPLE 8

Decahydro-3-[2-[(2,3-dihydro-1,4-benzodioxan-2-ylmethyl)amino]ethyl]-1,5-methano-6,7,9-metheno-2H-pentaleno[1,2d]azepine-2,4(3H)-dione To 2.1 g of 2-[2,3-dihydro-1,4-benzodioxan-2-ylmethyl)amino]ethylamine (10 mmoles) in 100 ml of xylene was added 2.3 g (10 mmole) decahydro-1,5-methano-6,8,9-methenopentaleno[1,2-d]oxepine-2,4(1H, 5H)-dione and the mixture was refluxed under nitrogen for 48 hours with water separation via a Dean-Stark trap. The mixture was concentrated in vacuum and the residue column chromatographed on 100 g silica gel using chloroform as eluent. Crystallization from isopropanol with addition of 4N isopropanolic HCl gave 0.82 g of hydrochloride (m.p. 208°–209° C.).

Elemental analysis for: $C_{25}H_{28}N_2O_4 \cdot HCl$
Calc'd: C, 65.71; H, 6.40; N, 6.13
Found: C, 65.44; H, 6.44; N, 6.05

What is claimed is:

1. A compound of the formula:

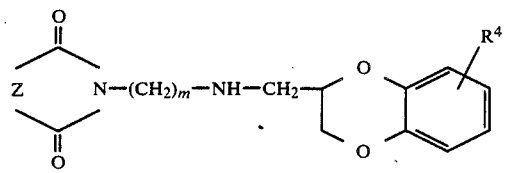

in which
Z is

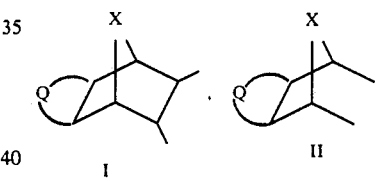

wherein
X is alkylene of 1 to 4 carbon atoms, ethenylene or alkylidene of 2 to 4 carbon atoms;
Q is alkylene of 1 to 4 carbon atoms, alkylidene of 2 to 4 carbon atoms,

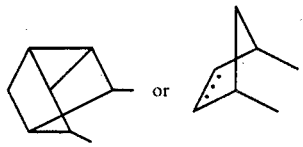

or Q, taken together with the carbon atoms to which its attached forms a benzene ring or a substituted benzene ring, in which the substituent is —OH, —OCH₃, alkyl of 1 to 3 carbon atoms, halo, —CF₃, —NH₂, monoalkylamino, in which the alkyl substituent contains 1 to 3 carbon atoms, dialkylamino in which each of the alkyl substituents contains 1 to 3 carbon atoms, or alkanoylamino in which said alkanoyl group contains 2 to 4 carbon atoms;

$R^1$ is hydrogen or alkyl of 1 to 3 carbon atoms;

$R^2$ and $R^3$ are, independently, hydrogen or alkyl of 1 to 3 carbon atoms, or taken together with the carbon atom to which they are attached, they form a cycloalkane or cycloalkene ring of 3 to 7 carbon atoms;

m is one of the integers 2, 3, 4, or 5;

$R^4$ is hydrogen, hydroxy, cyano, alkyl of 1 to 3 carbon atoms, alkoxy of 1 to 3 carbon atoms, halo, —$NHR^5$ where $R^5$ is H, alkyl of 1 to 3 carbon atoms, phenyl, tolyl, xylyl, mesityl, methoxyphenyl or halophenyl;

and the dotted line represents optional unsaturation; or a pharmaceutically acceptable salt thereof.

2. A compound of claim 1 of the formula:

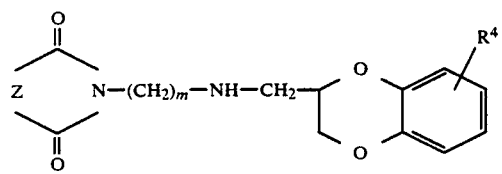

in which
Z is

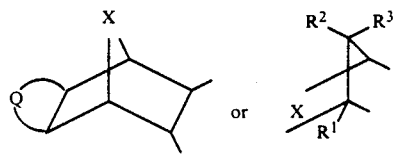

where
$Q, R^1, R^2, R^3$ and m are defined in claim 1;
X is ethylene or ethenylene;
and
$R^4$ is —H, —OH or —$OCH_3$; or a pharmaceutically acceptable salt thereof.

3. A compound of claim 1 of the formula:

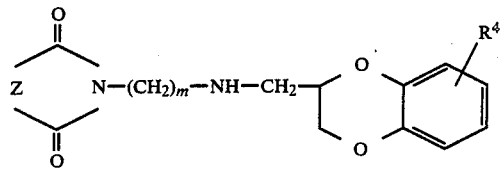

in which
Z is

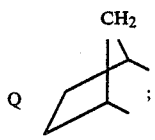

Q and m are defined in claim 1;
and
$R^4$ is hydrogen, hydroxy or methoxy; or a pharmaceutically acceptable salt thereof.

4. The compound of claim 1 which is decahydro-3-[4-[(2,3-dihydro-1,4-benzodioxan-2-ylmethyl)amino]butyl]-1,5-methano-6,7,9-metheno-2H-pentaleno[1,2-d]azepine-2,4(3H)-dione.

5. The compound of claim 1 which is endo-2-[4-[(2,3-dihydro-1,4-benzodioxan-2-ylmethyl)amino]butyl]octahydro-4,5,7-metheno-1H-pentaleno-[1,2-c]pyrrole-1,3(2H)-dione.

6. A compound of claim 1 which is exo-2-[4-[(2,3-dihydro-1,4-benzodioxan-2-ylmethyl)amino]butyl]octahydro-4,5,7-metheno-1H-pentaleno[1,2-c]pyrrole-1,3(2H)-dione.

7. A compound of claim 1 which is 2-[4-[(2,3-dihydro-1,4-benzodioxan-2-ylmethyl)amino]butyl]hexahydro-4,7-etheno-1H-cyclobut[f]isoindole-1,3-(2H)-dione.

8. A compound of claim 1 which is 2-[4-[2,3-dihydro-1,4-benzodioxan-2-ylmethyl)amino]butyl]hexahydro-4,6-etheno-cycloprop[f]isoindole-1,3-(2H,3aH)dione.

9. A compound of claim 1 which is 3-[2-[[(2,3-dihydro-1,4-benzodioxan-2-ylmethyl)amino]ethyl]-1,8,8-trimethyl-3-azabicyclo[3.2.1]octane-2,4-dione.

10. A compound of claim 1 which is 2-[2-[(2,3-dihydro-1,4-benzodioxan-2-ylmethyl)amino]ethyl]hexahydro-4,7-etheno-1H-cyclobut[f]isoindole-1,3-(2H)-dione.

11. A compound of claim 1 which is decahydro-3-[2-[(2,3-dihydro-1,4-benzodioxan-2-ylmethyl)amino]ethyl]-1,5-methano-6,7,9-metheno-2H-pentaleno[1,2-d]azepine-2,4(3H)-dione.

* * * * *